US007608265B2

(12) United States Patent
Burnie et al.

(10) Patent No.: US 7,608,265 B2
(45) Date of Patent: Oct. 27, 2009

(54) TREATMENT FOR BACTERIAL INFECTIONS

(75) Inventors: James Peter Burnie, Manchester (GB);
Ruth Christine Matthews, Manchester (GB); Tracey Carter, Manchester (GB)

(73) Assignee: NeuTec Pharma Ltd., Surrey (GB)

( * ) Notice: Subject to any disclaimer, the term of this patent is extended or adjusted under 35 U.S.C. 154(b) by 0 days.

(21) Appl. No.: 11/630,926

(22) PCT Filed: Jul. 1, 2005

(86) PCT No.: PCT/GB2005/002607

§ 371 (c)(1),
(2), (4) Date: Aug. 6, 2007

(87) PCT Pub. No.: WO2006/003426

PCT Pub. Date: Jan. 12, 2006

(65) Prior Publication Data

US 2008/0038266 A1 Feb. 14, 2008

(30) Foreign Application Priority Data

Jul. 2, 2004 (GB) ................................. 0414886.2

(51) Int. Cl.
*A61K 39/395* (2006.01)
*A61K 39/40* (2006.01)
*C07K 17/00* (2006.01)
(52) U.S. Cl. ................. 424/167.1; 424/130; 424/141.1; 424/150.1; 424/164.1; 530/350
(58) Field of Classification Search ........................ None
See application file for complete search history.

(56) References Cited

U.S. PATENT DOCUMENTS

| 6,291,158 | B1 | 9/2001 | Winter et al. |
| 6,667,035 | B1 | 12/2003 | Von Eichel-Streiber et al. |

FOREIGN PATENT DOCUMENTS

| EP | 0 368 684 | 5/1990 |
| EP | 0 376 851 | 7/1990 |
| WO | WO 91/09967 | 7/1991 |
| WO | WO 97/20932 | 6/1997 |
| WO | WO 00/12562 | 3/2000 |
| WO | WO 01/44300 | 6/2000 |
| WO | WO 01/27279 | 4/2001 |
| WO | WO 01/96599 | 12/2001 |
| WO | WO 02/055559 | 7/2002 |
| WO | WO 02/062379 | 8/2002 |
| WO | WO 03/048321 | 6/2003 |
| WO | WO 03/052416 | 6/2003 |
| WO | WO 2004/094474 | 11/2004 |

OTHER PUBLICATIONS

Wiesenborn et al. Applied and Environmental Microbiology, Nov. 1988, p. 2717-2722.*
Vajdos et al. (J. Mol. Biol. 2002. 320:415-428).*
De Pascalis et al (The Journal of Immunology. 2002 169: 3076-3084).*
MacCallum et al (J. Mol. Biol. 1996, 262: 732-745.*
Bendig (Methods: A Companion to Methods in Enzymology 1995; 8:83-93).*
Sliwkowski et al., "Incorporation and Distribution of Selenium Into Thiolase From Clostridium-Kluyveri", Journal of Biological Chemistry, 260(5): 3140-3144 (1985).
Winzer et al., "Differential Regulation of Two Thiolase Genes from Clostridum acetobutylicum DSM 792", Journal of Molecular Microbiology and Biotechnology 2(4): 531-541 (2000).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" *J. Cell Biology* 111:2129-2138 (1990).
Burgoon et al., "Cloning the Antibody Response in Humans with Inflammatory Central Nervous System Disease: Analysis of the Expressed IgG Repertoire in Subacute Schlerosing Panencephalitis Brain Reveals Disease-Relevant Antibodies That Recognize Specific Measles Virus Antigens" *J. Immunol.* 163(6):3496-3502 (1999).
Casset et al., "A peptide Mimetic of an anti-CD4 monoclonal antibody by rational design" *BBRC* 307:198-205 (2003).
Chen et al., "Selection and Analysis of an Optimized Anti-VEGF Antibody: Crystal Structure of an Affinity-matured Fab in Complex with Antigen" *J. Mol. Biol.* 293:865-881 (1999).
Colman "Effects of amino acid sequence changes on antibody-antigen interactions" *Res. in Immunol.* 145:33-36 (1994).
Currier et al., "Mitogens, Superantigens, and Nominal Antigens Elicit Distinctive Patterns of TCRB CDR3 Diversity" *Human Immunol.* 48:39-51 (1996).
Desiderio et al., "A Semi-synthetic Repertoire of Intrinsically Stable Antibody Fragments Derived from a Single-framework Scaffold" *J. Mol. Biol.* 310:603-615 (2001).
Holm et al., "Functional mapping and single chain construction of the anti-cytokeratin 8 monoclonal antibody TS1" *Mol. Immunol.* 44:1075-1084 (2007).
Holt et al., "Domain antibodies: proteins for therapy" *Trends in Biotechnology* 21(11):484-490 (2003).
Lazar et al , "Transforming Growth Factor α: Mutation of Aspartic Acid 47 and Leucine 48 Results • in Different Biological Activities" *Mol. Cell. Biol.* 8(3):1247-1252 (1988).
Lewis et al., "Use of a Novel Mutagenesis Strategy, Optimized Residue Substitution, to Decrease the Off-Rate of an Anti-gp120 Antibody" *Mol. Immunol.* 32(14/15):1065-1072 (1995).
Lin et al., "Structure-Function Relationships in Glucagon: Properties of Highly Purified Dis-His$^1$-, Monoiodo-, and [Des-Asn$^{28}$, Thr$^{29}$] (homoserine lactone$^{27}$)-glucagon" *Biochem. USA* 14:1559-1563 (1975).

(Continued)

*Primary Examiner*—Robert B Mondesi
*Assistant Examiner*—Oluwatosin Ogunbiyi
(74) *Attorney, Agent, or Firm*—Baker & Hostetler LLP

(57) ABSTRACT

The present invention is concerned with compounds, medicaments and treatments for *Clostridium difficile* infection, together with novel isolated antibodies and their use in same. The present invention is also concerned with the treatment and prophylaxis of *E. faecium* and *E. faecalis* infection and provides medicaments and treatments for same.

4 Claims, No Drawings

OTHER PUBLICATIONS

Nie et al.," Immunization with immune complex alters the repertoire of antigen-reactive B cells in the germinal centers" *Eur. J. Immunol.* 27(12):3517-3525 (1997).

Panka et al., "Variable region framework differences result in decreased or increased affinity of variant anti-digoxin antibodies" *PNAS USA* 85:3080-3084, 1988.

Rinaldi et al., "Antibodies Elicited by Naked DNA Vaccination Against the Complementary-determining Region 3 Hypervariable Region of Immunoglobulin Heavy Chain Idiotypic Determinants of B-lymphoproliferative Disorders Specifically React with Patients' Tumor Cells" *Cancer Res.* 61:1555-1568 (2001).

Rinaldi et al., "Strategies to Elicit Anti-Idiotypic Immune Response in B-Lymphoma Patients" *Gene Therapy of Cancer* edited by Walden et al. Plenum Press, New York, 323-330 (1998).

Rudikoff et al, "Single amino acid substitution altering antigen-binding specificity" *PNAS USA.,* 79(6):1979-1983 (1982).

Schwartz et al., "A superactive insulin: [B10-Aspartic acid]insulin(human)" *PNAS USA* 84:6408-6411 (1987).

Wen et al., "In-vivo immune response to idiotypic VH complementarity-determining region 3 peptide vaccination in B-cell non-Hodgkins lymphoma" *British J. Haematology* 103:663-668 (1998).

White et al, "Analysis of Immunoglobulin (Ig) Isotype Diversity and IgM/D Memory in the Response to Phenyl-Oxazolone" *J. Exp. Med.* 191(12):2209-2219 (2000).

* cited by examiner

SEQUENCE LISTING

<160> NUMBER OF SEQ ID NOS: 47

<210> SEQ ID NO 1
<211> LENGTH: 126
<212> TYPE: PRT
<213> ORGANISM: Homo sapiens

<400> SEQUENCE: 1

```
Glu Val Gln Leu Val Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
                20                  25                  30

Ser Tyr Ser Trp Ser Trp Ile Arg Gln Arg Pro Gly Gln Gly Leu Glu
            35                  40                  45

Trp Ile Gly Phe Ile Tyr Tyr Thr Gly Tyr Thr Ser Tyr Lys Ser Ser
    50                  55                  60

Leu Lys Ser Arg Val Ser Leu Ser Val Asp Thr Ser Asn Asp Gln Phe
65                  70                  75                  80

Ser Leu Ser Leu Ser Ser Val Thr Ala Ala Asp Thr Ala Val Tyr Tyr
                85                  90                  95

Cys Ala Arg Glu Ile Arg Ala Pro Asp His His Asp Phe Ser Gly Tyr
            100                 105                 110

Leu Gly Arg Trp Gly Gln Gly Thr Leu Val Thr Val Ser Ser
        115                 120                 125
```

```
<210> SEQ ID NO 2
<211> LENGTH: 12
<212> TYPE: PRT
<213> ORGANISM: Homo sapiens

<400> SEQUENCE: 2

Gly Gly Ser Val Ser Ser Gly Ser Tyr Ser Trp Ser
1               5                   10

<210> SEQ ID NO 3
<211> LENGTH: 16
<212> TYPE: PRT
<213> ORGANISM: Homo sapiens

<400> SEQUENCE: 3

Phe Ile Tyr Tyr Thr Gly Tyr Thr Ser Tyr Lys Ser Ser Leu Lys Ser
1               5                   10                  15

<210> SEQ ID NO 4
<211> LENGTH: 16
<212> TYPE: PRT
<213> ORGANISM: Homo sapiens

<400> SEQUENCE: 4

Glu Ile Arg Ala Pro Asp His His Asp Phe Ser Gly Tyr Leu Gly Arg
1               5                   10                  15

<210> SEQ ID NO 5
<211> LENGTH: 16
<212> TYPE: PRT
<213> ORGANISM: Homo sapiens

<400> SEQUENCE: 5

Glu Val Arg Ala Pro Asp His His Asp Phe Ser Gly Tyr Leu Gly Arg
1               5                   10                  15

<210> SEQ ID NO 6
<211> LENGTH: 16
<212> TYPE: PRT
<213> ORGANISM: Homo sapiens

<400> SEQUENCE: 6

Glu Asn Arg Ala Pro Asp His His Asp Phe Ser Gly Tyr Leu Gly Arg
1               5                   10                  15

<210> SEQ ID NO 7
<211> LENGTH: 16
<212> TYPE: PRT
<213> ORGANISM: Homo sapiens

<400> SEQUENCE: 7

Glu Ile Arg Ala Pro Asn His His Asp Phe Ser Gly Tyr Leu Gly Arg
1               5                   10                  15

<210> SEQ ID NO 8
<211> LENGTH: 16
<212> TYPE: PRT
<213> ORGANISM: Homo sapiens

<400> SEQUENCE: 8

Glu Ile Arg Ala Pro His His His Asp Phe Ser Gly Tyr Leu Gly Arg
1               5                   10                  15

<210> SEQ ID NO 9
```

```
<211> LENGTH: 16
<212> TYPE: PRT
<213> ORGANISM: Homo sapiens

<400> SEQUENCE: 9

Glu Ile Arg Ala Pro Asp His His His Phe Ser Gly Tyr Leu Gly Arg
1               5                   10                  15

<210> SEQ ID NO 10
<211> LENGTH: 16
<212> TYPE: PRT
<213> ORGANISM: Homo sapiens

<400> SEQUENCE: 10

Glu Ile Arg Ala Pro Asp His His Asp Tyr Ser Gly Tyr Leu Gly Arg
1               5                   10                  15

<210> SEQ ID NO 11
<211> LENGTH: 16
<212> TYPE: PRT
<213> ORGANISM: Homo sapiens

<400> SEQUENCE: 11

Glu Ile Arg Ala Pro Asp His His Asp Leu Ser Gly Tyr Leu Gly Arg
1               5                   10                  15

<210> SEQ ID NO 12
<211> LENGTH: 16
<212> TYPE: PRT
<213> ORGANISM: Homo sapiens

<400> SEQUENCE: 12

Glu Ile Arg Ala Pro Asp His His Asp Phe Ser Val Tyr Leu Gly Arg
1               5                   10                  15

<210> SEQ ID NO 13
<211> LENGTH: 13
<212> TYPE: PRT
<213> ORGANISM: Homo sapiens

<400> SEQUENCE: 13

Glu Ile Arg Ala Pro Asp His His Asp Phe Ser Leu Ser
1               5                   10

<210> SEQ ID NO 14
<211> LENGTH: 16
<212> TYPE: PRT
<213> ORGANISM: Homo sapiens

<400> SEQUENCE: 14

Glu Ile Arg Ala Pro Asp His His Asp Phe Ser Gly Tyr Pro Gly Arg
1               5                   10                  15

<210> SEQ ID NO 15
<211> LENGTH: 16
<212> TYPE: PRT
<213> ORGANISM: Homo sapiens

<400> SEQUENCE: 15

Glu Ile Arg Ala Pro Asp His His Asp Phe Ser Gly Tyr Leu Gly Cys
1               5                   10                  15

<210> SEQ ID NO 16
<211> LENGTH: 108
<212> TYPE: PRT
```

<213> ORGANISM: Homo sapiens

<400> SEQUENCE: 16

```
Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
            20                  25                  30
Ser Trp Tyr Gln Gln Lys Pro Gly Gln Ala Pro Val Leu Val Ile Tyr
        35                  40                  45
Gly Lys Asn Asn Arg Pro Ser Gly Ile Pro Asp Arg Phe Ser Gly Ser
    50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Thr Gly Asn Gln
                85                  90                  95
Leu Phe Gly Gly Gly Thr Lys Val Thr Val Leu Gly
            100                 105
```

<210> SEQ ID NO 17
<211> LENGTH: 11
<212> TYPE: PRT
<213> ORGANISM: Homo sapiens

<400> SEQUENCE: 17

```
Gln Gly Asp Ser Leu Arg Ser Tyr Tyr Ala Ser
1               5                   10
```

<210> SEQ ID NO 18
<211> LENGTH: 7
<212> TYPE: PRT
<213> ORGANISM: Homo sapiens

<400> SEQUENCE: 18

```
Gly Lys Asn Asn Arg Pro Ser
1               5
```

<210> SEQ ID NO 19
<211> LENGTH: 10
<212> TYPE: PRT
<213> ORGANISM: Homo sapiens

<400> SEQUENCE: 19

```
Asn Ser Arg Asp Ser Thr Gly Asn Gln Leu
1               5                   10
```

<210> SEQ ID NO 20
<211> LENGTH: 11
<212> TYPE: PRT
<213> ORGANISM: Homo sapiens

<400> SEQUENCE: 20

```
Asn Ser Arg Asp Asn Thr Gly His His Val Val
1               5                   10
```

<210> SEQ ID NO 21
<211> LENGTH: 11
<212> TYPE: PRT
<213> ORGANISM: Homo sapiens

<400> SEQUENCE: 21

```
Asn Ser Arg Asp Ser Ser Gly Asn His Val Val
1               5                   10
```

```
<210> SEQ ID NO 22
<211> LENGTH: 11
<212> TYPE: PRT
<213> ORGANISM: Homo sapiens

<400> SEQUENCE: 22

Ser Ser Arg Asp Asn Ser Gly Asp Arg Tyr Val
1               5                   10

<210> SEQ ID NO 23
<211> LENGTH: 10
<212> TYPE: PRT
<213> ORGANISM: Homo sapiens

<400> SEQUENCE: 23

His Ser Arg Asp Thr Asn Gly Asp His Leu
1               5                   10

<210> SEQ ID NO 24
<211> LENGTH: 10
<212> TYPE: PRT
<213> ORGANISM: Homo sapiens

<400> SEQUENCE: 24

Asn Ser Arg Asp Gly Thr Gly Asn Gln Leu
1               5                   10

<210> SEQ ID NO 25
<211> LENGTH: 10
<212> TYPE: PRT
<213> ORGANISM: Homo sapiens

<400> SEQUENCE: 25

Asn Ser Arg Asp Thr Asn Gly Asp Gln Leu
1               5                   10

<210> SEQ ID NO 26
<211> LENGTH: 11
<212> TYPE: PRT
<213> ORGANISM: Homo sapiens

<400> SEQUENCE: 26

Asn Ser Arg Asp Ser Ser Gly Asn Leu Gly Leu
1               5                   10

<210> SEQ ID NO 27
<211> LENGTH: 11
<212> TYPE: PRT
<213> ORGANISM: Homo sapiens

<400> SEQUENCE: 27

Asn Ser Arg Asp Ser Ser Gly Asn Leu Gly Val
1               5                   10

<210> SEQ ID NO 28
<211> LENGTH: 11
<212> TYPE: PRT
<213> ORGANISM: Homo sapiens

<400> SEQUENCE: 28

Asn Ser Arg Asp Ser Ser Gly Tyr His Val Ile
1               5                   10
```

```
<210> SEQ ID NO 29
<211> LENGTH: 11
<212> TYPE: PRT
<213> ORGANISM: Homo sapiens

<400> SEQUENCE: 29

Ser Ser Arg Asp Ser Lys Gly His Arg Tyr Val
1               5                   10

<210> SEQ ID NO 30
<211> LENGTH: 11
<212> TYPE: PRT
<213> ORGANISM: Homo sapiens

<400> SEQUENCE: 30

Ser Ser Arg Asp Ser Asn Gly Asn Arg Tyr Val
1               5                   10

<210> SEQ ID NO 31
<211> LENGTH: 11
<212> TYPE: PRT
<213> ORGANISM: Homo sapiens

<400> SEQUENCE: 31

Ser Ser Arg Asp Thr Lys Gly His Arg Tyr Val
1               5                   10

<210> SEQ ID NO 32
<211> LENGTH: 10
<212> TYPE: PRT
<213> ORGANISM: Homo sapiens

<400> SEQUENCE: 32

Lys Pro Arg Asp Ser Ser Gly Asn His Val
1               5                   10

<210> SEQ ID NO 33
<211> LENGTH: 10
<212> TYPE: PRT
<213> ORGANISM: Homo sapiens

<400> SEQUENCE: 33

Ser Arg Asp Ser Ser Gly His Val Ala Val
1               5                   10

<210> SEQ ID NO 34
<211> LENGTH: 12
<212> TYPE: PRT
<213> ORGANISM: Homo sapiens

<400> SEQUENCE: 34

Asn Ser Arg Asp Ser Ser Gly Asp Pro Leu Gly Val
1               5                   10

<210> SEQ ID NO 35
<211> LENGTH: 11
<212> TYPE: PRT
<213> ORGANISM: Homo sapiens

<400> SEQUENCE: 35

Ala Ser Arg Asp Ser Ser Gly His Val Ala Val
1               5                   10

<210> SEQ ID NO 36
<211> LENGTH: 11
```

```
<212> TYPE: PRT
<213> ORGANISM: Homo sapiens

<400> SEQUENCE: 36

Asn Ser Arg Asp Ser Ser Gly Asn Leu Gly Cys
1               5                   10

<210> SEQ ID NO 37
<211> LENGTH: 11
<212> TYPE: PRT
<213> ORGANISM: Homo sapiens

<400> SEQUENCE: 37

Asn Ser Arg Asp Ser Ser Gly Asn Leu Gly Trp
1               5                   10

<210> SEQ ID NO 38
<211> LENGTH: 11
<212> TYPE: PRT
<213> ORGANISM: Homo sapiens

<400> SEQUENCE: 38

Ser Ser Arg Asp Arg Asn Gly His Arg Tyr Val
1               5                   10

<210> SEQ ID NO 39
<211> LENGTH: 11
<212> TYPE: PRT
<213> ORGANISM: Homo sapiens

<400> SEQUENCE: 39

Ser Ser Arg His Thr Lys Gly His Arg Tyr Val
1               5                   10

<210> SEQ ID NO 40
<211> LENGTH: 11
<212> TYPE: PRT
<213> ORGANISM: Homo sapiens

<400> SEQUENCE: 40

Thr Ser Arg Asp Ser Asn Gly Asn Arg Tyr Val
1               5                   10

<210> SEQ ID NO 41
<211> LENGTH: 250
<212> TYPE: PRT
<213> ORGANISM: Artificial sequence
<220> FEATURE:
<223> OTHER INFORMATION: synthetic H1L1 antibody

<400> SEQUENCE: 41

Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Ser Trp Ser Trp Ile Arg Gln Arg Pro Gly Gln Gly Leu Glu
        35                  40                  45

Trp Ile Gly Phe Ile Tyr Tyr Thr Gly Tyr Thr Ser Tyr Lys Ser Ser
    50                  55                  60

Leu Lys Ser Arg Val Ser Leu Ser Val Asp Thr Ser Asn Asp Gln Phe
65                  70                  75                  80

Ser Leu Ser Leu Ser Ser Val Thr Ala Ala Asp Thr Ala Val Tyr Tyr
                85                  90                  95
```

-continued

```
Cys Ala Arg Glu Ile Arg Ala Pro Asp His His Asp Phe Ser Gly Tyr
            100                 105                 110
Leu Gly Arg Trp Gly Gln Gly Thr Leu Val Thr Val Ser Ser Gly Gly
        115                 120                 125

Ser Gly Gly Gly Gly Ser Gly Gly Gly Gly Ser Ala Ser Lys Ser Ser
    130                 135                 140
Glu Leu Thr Gln Asp Pro Ala Val Ser Val Ala Leu Gly Gln Thr Val
145                 150                 155                 160
Arg Ile Thr Cys Gln Gly Asp Ser Leu Arg Ser Tyr Tyr Ala Ser Trp
                165                 170                 175
Tyr Gln Gln Lys Pro Gly Gln Ala Pro Val Leu Val Ile Tyr Gly Lys
            180                 185                 190
Asn Asn Arg Pro Ser Gly Ile Pro Asp Arg Phe Ser Gly Ser Ser Ser
        195                 200                 205
Gly Asn Thr Ala Ser Leu Thr Ile Thr Gly Ala Gln Ala Glu Asp Glu
    210                 215                 220
Ala Asp Tyr Tyr Cys Asn Ser Arg Asp Ser Thr Gly Asn Gln Leu Phe
225                 230                 235                 240
Gly Gly Gly Thr Lys Val Thr Val Leu Gly
                245                 250

<210> SEQ ID NO 42
<211> LENGTH: 22
<212> TYPE: PRT
<213> ORGANISM: Artificial sequence
<220> FEATURE:
<223> OTHER INFORMATION: putative sequence of antibody target
<220> FEATURE:
<221> NAME/KEY: MISC_FEATURE
<222> LOCATION: (12)..(15)
<223> OTHER INFORMATION: any amino acid

<400> SEQUENCE: 42

Ala Asn Ile Thr Pro Asp Met Ile Asp Glu Ser Xaa Xaa Xaa Xaa Val
1               5                   10                  15
Leu Thr Ala Gly Leu Gly
            20

<210> SEQ ID NO 43
<211> LENGTH: 412
<212> TYPE: PRT
<213> ORGANISM: Clostridium difficile
<220> FEATURE:
<221> NAME/KEY: MISC_FEATURE
<222> LOCATION: (62)..(88)
<223> OTHER INFORMATION: match with SEQ ID NO: 42

<400> SEQUENCE: 43

Ile Lys Leu Phe Lys Lys Gln Phe Arg Ile Tyr Glu Lys Ser Asn Leu
1               5                   10                  15

Met Gly Val Met Asn Met Arg Glu Val Val Ile Ala Ser Ala Ala Arg
            20                  25                  30

Thr Ala Val Gly Ser Phe Gly Gly Ala Phe Lys Ser Val Ser Ala Val
        35                  40                  45

Glu Leu Gly Val Thr Ala Ala Lys Glu Ala Ile Lys Arg Ala Asn Ile
    50                  55                  60

Thr Pro Asp Met Ile Asp Glu Ser Leu Leu Gly Gly Val Leu Thr Ala
65                  70                  75                  80

Gly Leu Gly Gln Asn Ile Ala Arg Gln Ile Ala Leu Gly Ala Gly Ile
```

-continued

```
                        85                  90                  95
Pro Val Glu Lys Pro Ala Met Thr Ile Asn Ile Val Cys Gly Ser Gly
            100                 105                 110
Leu Arg Ser Val Ser Met Ala Ser Gln Leu Ile Ala Leu Gly Asp Ala
        115                 120                 125
Asp Ile Met Leu Val Gly Gly Ala Glu Asn Met Ser Met Ser Pro Tyr
    130                 135                 140
Leu Val Pro Ser Ala Arg Tyr Gly Ala Arg Met Gly Asp Ala Ala Phe
145                 150                 155                 160
Val Asp Ser Met Ile Lys Asp Gly Leu Ser Asp Ile Phe Asn Asn Tyr
                165                 170                 175
His Met Gly Ile Thr Ala Glu Asn Ile Ala Glu Gln Trp Asn Ile Thr
            180                 185                 190
Arg Glu Glu Gln Asp Glu Leu Ala Leu Ala Ser Gln Asn Lys Ala Glu
        195                 200                 205
Lys Ala Gln Ala Glu Gly Lys Phe Asp Glu Glu Ile Val Pro Val Val
    210                 215                 220
Ile Lys Gly Arg Lys Gly Asp Thr Val Val Asp Lys Asp Glu Tyr Ile
225                 230                 235                 240
Lys Pro Gly Thr Thr Met Glu Lys Leu Ala Lys Leu Arg Pro Ala Phe
                245                 250                 255
Lys Lys Asp Gly Thr Val Thr Ala Gly Asn Ala Ser Gly Ile Asn Asp
            260                 265                 270
Gly Ala Ala Met Leu Val Val Met Ala Lys Glu Lys Ala Glu Glu Leu
        275                 280                 285
Gly Ile Glu Pro Leu Ala Thr Ile Val Ser Tyr Gly Thr Ala Gly Val
    290                 295                 300
Asp Pro Lys Ile Met Gly Tyr Gly Pro Val Pro Ala Thr Lys Lys Ala
305                 310                 315                 320
Leu Glu Ala Ala Asn Met Thr Ile Glu Asp Ile Asp Leu Val Glu Ala
                325                 330                 335
Asn Glu Ala Phe Ala Ala Gln Ser Val Ala Val Ile Arg Asp Leu Asn
            340                 345                 350
Ile Asp Met Asn Lys Val Asn Val Asn Gly Gly Ala Ile Ala Ile Gly
        355                 360                 365
His Pro Ile Gly Cys Ser Gly Ala Arg Ile Leu Thr Thr Leu Leu Tyr
    370                 375                 380
Glu Met Lys Arg Arg Asp Ala Lys Thr Gly Leu Ala Thr Leu Cys Ile
385                 390                 395                 400
Gly Gly Gly Met Gly Thr Thr Leu Ile Val Lys Arg
                405                 410
```

<210> SEQ ID NO 44
<211> LENGTH: 19
<212> TYPE: DNA
<213> ORGANISM: Artificial sequence
<220> FEATURE:
<223> OTHER INFORMATION: PCR primer

<400> SEQUENCE: 44
atgagagaag tagtaattg                                               19

<210> SEQ ID NO 45
<211> LENGTH: 20
<212> TYPE: DNA
<213> ORGANISM: Artificial sequence -continued
<220> FEATURE:
<223> OTHER INFORMATION: PCR primer

<400> SEQUENCE: 45
tctcttaact attaaagtag                                                  20

<210> SEQ ID NO 46
<211> LENGTH: 765
<212> TYPE: DNA
<213> ORGANISM: Artificial sequence
<220> FEATURE:
<223> OTHER INFORMATION: coding sequence for antibody H1L1

<400> SEQUENCE: 46
tgaggtgcag ctggtggagt ctggcccagg actggtgaag ccttcggaga ccctgtccct      60
cacctgcact gtctctggtg gctccgtcag cagtggtagt tactcttgga gctggatccg     120
ccagcgccca ggacagggcc tggagtggat tgggttcatc tactacactg gtacacctc     180 ctacaagtcg tccctcaaga gtcgagtctc cctgtcggtt gacacgtcta acgaccagtt    240
ctccctgagc ctgagctctg taactgccgc ggacacggcc gtgtattact gtgcgaggga    300
aattcgtgcc ccagatcacc atgattttag tggttatctc ggccgctggg gccagggaac    360
cctggtcacc gtctcctcag gcgcgccggg tggtggcggc agcggtggcg gtggcagcgg    420
tggcggcggt agcgctagct tcttctgagc tgactcagga ccctgctgtg tctgtggcct    480
tgggacagac agtcaggatc acatgccaag gagacagcct cagaagctat tatgcaagct    540
ggtaccagca gaagccagga caggcccctg tacttgtcat ctatggtaaa aacaaccggc    600
cctcagggat cccagaccga ttctctggct ccagctcagg taacacagct tccttgacca    660
tcactggggc gcaggcggaa gatgaggctg actactactg taactcccgg gacagcactg    720
gtaaccagct gttcggcgga gggaccaagg tcaccgtcct aggta                    765

<210> SEQ ID NO 47
<211> LENGTH: 4
<212> TYPE: PRT
<213> ORGANISM: Clostridium difficile
<220> FEATURE:
<221> NAME/KEY: MISC_FEATURE
<222> LOCATION: (1)..(4)
<223> OTHER INFORMATION: C.difficile thiolase conserved epitope

<400> SEQUENCE: 47

Val Val Ile Ala
1

TREATMENT FOR BACTERIAL INFECTIONS

CROSS-REFERENCE TO RELATED APPLICATIONS

This application is the National Stage of International Application No. PCT/GB2005/002607, filed on Jul. 1, 2005, which claims the benefit of United Kingdom Patent Application No. GB0414886.2, filed on Jul. 2, 2004. The contents of both of these applications are incorporated herein by reference in their entireties.

The present invention is concerned with compounds, medicaments and treatments for *Clostridium difficile* infection, together with novel isolated antibodies and their use in same. The present invention is also concerned with the prophylaxis and treatment of *E. faecium* and *E. faecalis* infection and provides medicaments and treatments for same.

*C. difficile* is a gram-positive anaerobic bacterium, and is deemed a significant human pathogen causing a spectrum of diseases ranging from mild diarrhoea to fulminant pseudomembranous colitis (PMC)—collectively referred to as *C. difficile* antibiotic-associated diarrhoea (CDAD). CDAD is a common, iatrogenic, nosocomial disease associated with substantial morbidity and mortality, especially in the elderly. Two factors have been assigned main roles in the pathogenesis of CDAD—the suppression of the resident intestinal flora by the administration of antibiotics, and the production by the bacterium of two high molecular weight toxins, exotoxin A and exotoxin B.

The bacterium is endemic in hospitals, and studies have shown that approximately one third of patients receiving antibiotic treatment in acute-care medical wards were colonised by *C. difficile* while in hospital (Kyne, L., et al., 2002, Clin. Infect. Dis. 34(3), pp 346-53, PMID: 11774082). Of these patients, over half went on to develop CDAD while the remainder were symptomless carriers. CDAD is a major factor in extension of patient hospital stay times, and estimates suggest that the cost of this disease in the US exceeds $1.1 billion per year (Kyne, L., et al., Supra). Patients suffering from CDAD respond well to a treatment which includes a discontinuation of the inciting antibiotic and treatment with either of the antibiotics metronidazole and vancomycin. The response rate to initial antibiotic therapy can be high (up to 95%), but up to 20% of patients can relapse within one or two weeks of a first treatment, with the risk of relapse compounding with each relapse episode. Relapse can typically be treated with antibiotics, indicating that it is due to infection with different *C. difficile* strains. Additionally, there is evidence that *C. difficile* is becoming resistant to metronidazole and partially resistant to vancomycin, demonstrating the need for new alternatives in the treatment of CDAD.

Exotoxins A and B which are produced by pathogenic strains of the bacterium are cytotoxic, enterotoxic and proinflammatory, and are considered to be the main virulence factors of this non-invasive microorganism. However, not all infections with toxigenic strains result in disease, prompting the search for additional virulence factors. Bacterial surface expressed antigens represent candidate virulence factors, and are also considered important since such proteins likely mediate the essential functions such as adhesion to the epithelial layer of the gut in the first step of colonization or interaction with mediators of local immunity. In common with many other bacteria, *C. difficile* expresses a crystalline or paracrystalline surface layer (S-layer) on the outer cell surface. Such S-layers comprise proteins or glycoproteins forming a regularly arranged lattice on the external surface of the bacterium, and have previously been shown to be essential for the virulence of pathogens such as *Aeromanas salmonicida* and *Campylobacter fetus*. In contrast to most bacteria which comprise one S-layer, *C. difficile* is known to comprise two superimposed paracrystalline S-layers, each composed of a glycoprotein subunit which varies slightly in apparent molecular weight among different *C. difficile* strains. Most strains of *C. difficile* express two major S-layer proteins (SLPs), one of 32-38 kDa (low-MW SLP) and a second of 42-48 kDa (high-MW SLP). The low-MW SLP appears to be immunodominant and is the antigen most commonly recognised by patients suffering from CDAD, and is the only antigen recognised in EDTA extracts of bacteria by antisera raised in rabbits against whole *C. difficile* cells (Calabi, E. et al., 2001, Mol. Microbiol., 40(5) p 1187-99, PMID: 11401722).

During the course of microbial infection various adaptive strategies are employed by the immune system. One such strategy, and arguably the most important, is the production of an antibody response. Antibodies capable of binding antigens displayed by the infectious agent are produced and bind to and allow killing of the microorganism through complement activation, recruitment of macrophage and through direct interaction with the microbe itself. The therapeutic efficacy of antibodies capable of binding a given antigen varies and this is reflected in the fact that antibody production by the immune system matures during the course of an infection and becomes focussed in the case of a patient successfully fighting off an infection.

The antibody response is elicited by the B cell repertoire where individual B cells each produce structurally diverse antibody molecules. The actual size of this B cell/antibody repertoire is unknown, but it is estimated that the random clonal frequency of reactivity for a given antigen may be as high as 1 in 100,000 in cultured B cells (Nobrega, A., et al., Eur J. Immunol. 1998 April; 28(4):1204-15; PMID: 9565360). During the course of infection, antibodies capable of binding the pathogen are selected for by changes in the B cell population resulting in key antibodies being produced in large numbers. The mechanisms for these changes include clonal expansion, isotype switching, and somatic mutation of immunoglobulin variable regions. B cells responsible for generating antibodies which are able to bind a pathogen multiply, thus skewing the B cell repertoire and changing the proportions of B cells.

Antibody specific against the cell-binding domain of the *C. difficile* exotoxin A is found to be protective in a mouse model, and patients colonized with *C. difficile* but asymptotic for it are found to have an elevated anti-exotoxin A IgG titer. Infected patients developing such elevated serum anti-exotoxin A IgG titers in response to colonization are 48 times less likely to suffer from CDAD than patients who did not develop such an elevated titer. Therefore vaccination with *C. difficile* exotoxin A is suggested as a therapeutic strategy, as is the use of anti-*C. difficile* exotoxin A antibodies (Giannasca P J and Warny M., Vaccine, 2004 Feb. 17; 22(7): 848-56; PMID: 15040937).

Non-antibiotic based therapeutic regimes for the treatment/prevention of *C. difficile* infection are based upon vaccination and passive immunization. Vaccination treatment comprises administering to a patient either a nucleic acid sequence encoding an immunogenic fragment of the *C. difficile* surface layer protein or a variant or homologue thereof, or an equivalent polypeptide fragment (as disclosed in WO 02/062379). Passive immunotherapy is typically achieved by administering to a patient a monoclonal antibody specific to an immunogen produced by a pathogen. In general, passive immunotherapy is particularly effective in treating immunocompromised patients who are unable to respond to vaccination, and to patients who need immediate therapy and cannot wait for vaccination to take effect. In the case of a *C. difficile* infection, passive immunization relies on the administration to a patient of toxin-neutralizing polyclonal immune globulin, (as disclosed in WO 99/20304), or antibodies raised against the whole bacterium and the toxins (as disclosed in WO 96/07430).

Therefore the effective treatment of *C. difficile* infection is highly important, and the prior art teaches that the target for such therapy should be vaccination or passive immunotherapy targeted against the *C. difficile* exotoxin A, against the surface layer protein, or as a polyclonal serum specific against unidentified bacterial toxins.

However, the present inventor has identified a specific target for therapy. The experiments below show that patients infected with *C. difficile* produce an elevated titre of antibodies specific against acetyl-CoA acetyltransferase (thiolase), and that anti-acetyl-CoA acetyltransferase (thiolase) antibody per se is useful and effective in treating *C. difficile* infection. Furthermore, anti-acetyl-CoA acetyltransferase antibody, particularly a synthetic antibody constructed from the most dominant CDR sequences from *C. difficile* infected patients, when used together with the antibiotics vancomycin or gentamicin, results in synergistic therapy of *C. difficile* infection.

Thus according to a first aspect of the present invention there is provided the use of an inhibitor of acetyl-CoA acetyltransferase in the manufacture of a medicament for the treatment or prophylaxis of infection by *Clostridium difficile*.

As used herein, the term "treatment" is intended to have a broad meaning unless explicitly stated otherwise. Thus by "treatment" or "therapy" is meant any treatment which is designed to cure, alleviate, remove or lessen the symptoms of, or prevent or reduce the possibility of contracting disorders or malfunctions of the human or animal body. Thus by the term "treatment" is meant both treatment of disease conditions, as well as their prophylaxis.

In particular, the acetyl-CoA acetyltransferase may be from *Clostridium difficile*, and it may have the sequence of SEQ ID NO: 43.

A wide range of inhibitors may be used which are specific against the acetyl-CoA acetyltransferase. In particular, the acetyl-CoA acetyltransferase may form a specific binding pair (sbp) with the inhibitor, the acetyl-CoA acetyltransferase being the first member of the pair, and the inhibitor being the second member.

Herein, a "Member of a Specific Binding Pair" is one of two different molecules, having an area on the surface or in a cavity which specifically binds to and is thereby defined as complementary with a particular spatial and polar organization of the other molecule. The members of the specific binding pair are referred to as ligand and receptor (antiligand), sbp member and sbp partner, sbp members or the like. These are usually members of an immunological pair such as antigen-antibody, although the term does have a broader meaning encompassing other specific binding pairs, such as RNA-protein, DNA-protein, and the like.

Thus the inhibitor may be an antibody or an antigen binding fragment thereof, and it may be specific against an epitope displayed by the peptide of SEQ ID NO: 47

As detailed below in the Experiments section, the epitope displayed by the peptide having the sequence of SEQ ID NO: 47 has been identified as being conserved between various antigens and is therefore identified as being the peptide displaying the conserved epitope shared by those antigens.

The term "antibody" in its various grammatical forms is used herein to refer to immunoglobulin molecules and immunologically active portions of immunoglobulin molecules, i.e. molecules that contain an antibody combining site or paratope. Such molecules are also referred to as "antigen binding fragments" of immunoglobulin molecules.

Illustrative antibody molecules are intact immunoglobulin molecules, substantially intact immunoglobulin molecules and those portions of an immunoglobulin molecule that contain the paratope, including those portions known in the art as Fab, Fab', F(ab')2, scFv and F(v). Antibodies, their production and use are well known in the art (e.g. Harlow, E. and Lane, D., "Using Antibodies: A Laboratory Manual", Cold Spring Harbor Laboratory Press, New York, 1998).

As detailed in the experiments below, the variable heavy (VH) and variable light (VL) chains of antibodies produced by patients infected with *C. difficile* have been cloned and sequenced and their complementarity determining regions (CDRs) identified. This has shown that there are highly immunodominant VH chain CDRs 1-3 (CDR-H1, CDR-H2 and CDR-H3), and highly immunodominant VL chain CDRs 1-3 (CDR-L1, CDR-L2 and CDR-L3).

Thus, the antibody or antigen binding fragment thereof may have VH chain complementarity determining regions (CDRs) 1-3 having the sequences of SEQ ID NOs: 2-4 respectively. In particular, the antibody or antigen binding fragment thereof may have a VH chain having the sequence of SEQ ID NO: 1.

Similarly, the antibody or antigen binding fragment thereof may have VL chain complementarity determining regions (CDRs) 1-3 having the sequences of SEQ ID NOs: 17-19. In particular, the antibody or antigen binding fragment thereof may have a VL chain having the sequence of SEQ ID NO: 16.

A synthetic antibody having the above sequences has been created and used, and thus the antibody may have the sequence of SEQ ID NO: 41. The antibody detailed below having SEQ ID NO: 41 also comprises an N-terminal S-Tag and a C-terminal His-Tag. The tags are useful for experimental purposes but are unnecessary for the therapeutic antibody, although they (or other tags) may be considered useful. Thus the antibody may e.g. additionally comprise a His-Tag, for example a C-terminal His-Tag.

The experiments below have shown that not only is an inhibitor of acetyl-CoA acetyltransferase effective on its own in effecting treatment of *Clostridium difficile* infection, but it is also useful when used in conjunction with existing antibiotics, particularly gentamicin and vancomycin, and that such use can provide synergistic results. Preliminary experimental results also show that synergy is achieved with metronidazole.

Thus, the medicament may additionally comprise at least one of the group of antibiotics consisting: gentamicin, vancomycin and metronidazole.

Naturally, medical formulations of the present invention may comprise a pharmaceutically acceptable carrier, diluent or excipient (Remington's Pharmaceutical Sciences and US Pharmacopoeia, 1984, Mack Publishing Company, Easton, Pa., USA; United States Pharmacopoeia, ISBN: 1889788031).

As detailed above, an inhibitor of acetyl-CoA acetyltransferase effective on its own in effecting treatment of *Clostridium difficile* infection. Thus also provided according to the present invention is isolated and/or purified antibody comprising at least one of the group consisting:

(i) VH chain complementarity determining regions (CDRs) 1-3 having the sequences of SEQ ID NOs: 2-4 respectively; and (ii) VL chain complementarity determining regions (CDRs) 1-3 having the sequences of SEQ ID NOs: 17-19.

As above, the VH chain may have the sequence of SEQ ID NO: 1. The VL chain may have the sequence of SEQ ID NO: 16. The antibody may have the sequence of SEQ ID NO: 41.

Also provided is a nucleic acid molecule coding for such an antibody. The nucleic acid molecule may be isolated and/or purified. In particular, the nucleic acid molecule may have the sequence of SEQ ID NO: 46.

Also provided according to the present invention is the use of an inhibitor of acetyl-CoA acetyltransferase and vancomycin in the manufacture of a medicament for the prophylaxis or treatment of infection by *Enterococcus faecium*, or *Enterococcus faecalis*, particularly vancomycin resistant *Enterococcus faecium*.

The experiments below show that not only does the use of an inhibitor of acetyl-CoA acetyltransferase and vancomycin result in synergistic therapy of *C. difficile* infection, but it also results in synergistic therapy of *E. faecium* infection, particularly vancomycin resistant *E. faecium* infection. Preliminary experiments have also shown that synergy is also observed in the treatment of *E. faecalis* infection.

The acetyl-CoA acetyltransferase may be from *Clostridium difficile*.

The inhibitor may be an antibody or an antigen binding fragment thereof, and it may be specific against an epitope displayed by the peptide having the sequence of SEQ ID NO: 47.

As with other aspects of the present invention, the antibody or antigen binding fragment thereof may have VH chain complementarity determining regions (CDRs) 1-3 having the sequences of SEQ ID NOs: 2-4 respectively. The antibody or antigen binding fragment thereof VH chain may have the sequence of SEQ ID NO: 1.

The antibody or antigen binding fragment thereof may have VL chain complementarity determining regions (CDRs) 1-3 having the sequences of SEQ ID NOs: 17-19. The antibody or antigen binding fragment thereof VL chain may have the sequence of SEQ ID NO: 16.

The antibody or antigen binding fragment thereof may have the sequence of SEQ ID NO: 41.

Where the present invention is concerned with the provision of medicaments containing two or more active ingredients (for example antibody and an antibiotic), the present invention also provides combined preparations comprising such active ingredients. For example, two-pack preparations may be provided.

Thus also provided according to the present invention is a combined preparation for the treatment of infection by *Clostridium difficile*, comprising:
(i) an inhibitor of acetyl-CoA acetyltransferase; and
(ii) at least one of the group of antibiotics consisting: gentamicin, vancomycin, and metronidazole.

Also provided is a combined preparation for the treatment of infection by *Enterococcus faecium* or *Enterococcus faecalis*, comprising:
(i) an inhibitor of acetyl-CoA acetyltransferase; and
(ii) vancomycin.

The *Enterococcus faecium* or *Enterococcus faecalis* may be vancomycin resistant.

The present invention also extends to methods of treatment of patients. Thus also provided according to the present invention is a method of treatment of infection by *Clostridium difficile*, comprising administering a therapeutically effective quantity of an inhibitor of acetyl-CoA acetyltransferase to a patient in need of same. The method may additionally comprise administering a therapeutically effective quantity of at least one of the group of antibiotics consisting: gentamicin, vancomycin and metronidazole.

Also provided according to the present invention is a method of treatment of infection by *Enterococcus faecium* or *Enterococcus faecalis*, comprising administering a therapeutically effective quantity of:
(i) an inhibitor of acetyl-CoA acetyltransferase; and
(ii) vancomycin to a patient in need of same.

The *Enterococcus faecium* may be vancomycin resistant.

The invention will be further apparent from the following description, which show, by way of example only, forms of treatment of *C. difficile* and *E. faecium* infection.

EXPERIMENTS

In the experiments below, a synthetic antibody has been constructed using the most predominant VH and VL antibody sequences from patients infected with *C. difficile*, Using this synthetic antibody, an antigen was isolated and purified and electrospray mass spectrometry used to determine a putative partial sequence for the isolated protein. Searching of *C. difficile* genomic sequences for matches identified a possible candidate matching sequence. A comparison of the candidate *C. difficile* sequence identified a number of homologous proteins which are classified as acetyl-CoA acetyltransferase (thiolase) enzymes and confirms it as a member of that family. The closest match is NP_349376 from *Clostridium acetobutylicum*, which showed a 68% homology over 391 amino acids. Cloning, expression and purification of the candidate protein gave a protein which bound strongly with the synthetic antibody. Further experiments have shown that the antibody specific against the *C. difficile* acetyl-CoA acetyltransferase (thiolase) shows synergy with vancomycin and gentamicin in treating *C. difficile* infections. Preliminary experiments also show that synergy can also be achieved with metronidazole.

Experiments also show synergy between the synthetic antibody and vancomycin in the treatment of vancomycin resistant *E. faecium*. Preliminary experiments (not shown) also indicate synergy between the synthetic antibody and vancomycin in the treatment of *E. faecalis* infection.

Unless stated otherwise, all procedures were performed using standard protocols and following manufacturer's instructions where applicable. Standard protocols for various techniques including PCR, molecular cloning, manipulation and sequencing, the manufacture of antibodies, epitope mapping and mimotope design, cell culturing and phage display, are described in texts such as McPherson, M. J. et al. (1991, PCR: A practical approach, Oxford University Press, Oxford), Sambrook, J. et al. (1989, Molecular cloning: a laboratory manual, Cold Spring Harbour Laboratory, New York), Huynh and Davies (1985, "DNA Cloning Vol I—A Practical Approach", IRL Press, Oxford, Ed. D. M. Glover), Sanger, F. et al. (1977, PNAS USA 74(12): 5463-5467), Harlow, E. and Lane, D. ("Using Antibodies: A Laboratory Manual", Cold Spring Harbor Laboratory Press, New York, 1998), Jung, G. and Beck-Sickinger, A. G. (1992, Angew. Chem. Int. Ed. Eng., 31: 367-486), Harris, M. A. and Rae, I. F. ("General Techniques of Cell Culture", 1997, Cambridge University Press, ISBN 0521 573645), "Phage Display of Peptides and Proteins: A Laboratory Manual" (Eds. Kay, B. K., Winter, J., and McCafferty, J., Academic Press Inc., 1996, ISBN 0-12-402380-0).

Reagents and equipment useful in, amongst others, the methods detailed herein are available from the likes of GE Healthcare Bio-Sciences Corp. (formerly Amersham) of Piscataway, N.J. 08855-1327, U.S.A., Boehringer Mannheim of Ingelheim, Germany, Clontech of Mountain View, Calif. U.S.A., Sigma-Genosys (formerly Genosys) of The Woodlands, Tex. 77380-3600, U.S.A., Millipore of Billerica, Mass. 01821, U.S.A., Novagen of Gibbstown, N.J. 08027, U.S.A., Perkin Elmer of Waltham, Mass. 02451, U.S.A., Pfizer (formerly Pharmacia) of New York, N.Y. 10017, U.S.A., Promega of Madison, Wis. 53711, U.S.A., Qiagen Valencia, Calif. 91355, U.S.A., Sigma St. Louis, Mo. 63103, U.S.A. and Stratagene La Jolla, Calif. 92037, U.S.A.

The contents of each of the references discussed herein, including the references cited therein, are herein incorporated by reference in their entirety.

Where "PMID:" reference numbers are given for publications, these are the PubMed identification numbers allocated to them by the US National Library of Medicine, from which full bibliographic information and abstract for each publication is available via the Internet at the US National Library of Medicine Web site. This can also provide direct access to electronic copies of the complete publications, particularly in the case of e.g. PNAS, JBC and MBC publications.

Sequence homology is as determined using the BLAST2 program (Tatusova T. A. et al., FEMS Microbiol Lett. 1999 May 15; 174(2):247-50; PMID: 10339815) at the National Center for Biotechnology Information, USA (via the US National Library of Medicine Web site) with default parameters.

Identifying Dominant VH and VL Antibody Sequences from Patients Infected with *C. difficile*

In order to identify antibody sequences from patients with *C. difficile* infections and determine the dominant antibody sequences, particularly CDR sequences, the methods detailed in WO 03/052416 were used. B cells producing antibodies were identified, sequenced of and analysed, using the following basic steps (see WO 03/052416):

(1) Isolation of VH and/or VL coding regions from circulatory B cells of human patients.
(2) Determining the Nucleotide sequence of VH and/or VL repertoires.
(3) Determination of VH and/or VL primary amino acid sequences.
(4) Extraction of CDR regions in silico—incorporation into the database
(5) Detection of dominant CDR & framework regions in VH and/or VL repertoire.
(6) Construction and Production of therapeutic recombinant antibodies from dominant antibody sequences.

Fragments of antibodies were sequenced from four infected patients (D01, D02, D03 and D04).

Heavy Chain (CDH1)

CDH1 was the most commonly occurring VH chain from the *C. difficile* infected patients. It was identified from analysis of the CDR3 sequences from patient antibody VH chains. 226/1011 (22.4%) of cloned antibodies from *C. difficile* infected patients had the same CDR3 sequence (CDR-H3, below). CDH1 was found to be present in three quarters of patients. Its CDR3 sequence appeared in 184/318 (57.9%) of the clones from patient D01; in D03 it appeared in 40/291 (13.7%) of the clones; and in D04 it appeared in 2/252 (0.8%) of the clones. The most common full VH sequence is SEQ ID NO: 1.

Within this VH chain sequence, the CDR (complementarity determining region) sequences are as follows:

| | |
|---|---|
| CDR-H1 | SEQ ID NO: 2 |
| CDR-H2 | SEQ ID NO: 3 |
| CDR-H3 | SEQ ID NO: 4 |

Homology searches have identified several other CDR3 sequences with greater than 70% homology to the CDR-H3 sequence (SEQ ID NO: 4), all from *C. difficile* patients. The CDR3 sequences are SEQ ID NOs: 5-15.

Light Chain (CDL1)

The light chain for H1L1 was derived from a clone with the most common CDR3 sequence from *C. difficile* infected patients. CDL1 was present in patient D01 at a frequency of 84/251 (33.5%). The most common VL sequence containing this CDR3 sequence was SEQ ID NO: 16.

Within this VL chain sequence, the CDR (complementarity determining region) sequences are as follows:

| | |
|---|---|
| CDR-L1 | SEQ ID NO: 17 |
| CDR-L2 | SEQ ID NO: 18 |
| CDR-L3 | SEQ ID NO: 19 |

Homology searches have identified several other CDR3 sequences with greater than 70% homology to the CDR-L3 sequence, all from *C. difficile* patients. The CDR3 sequences are SEQ ID NOs: 20-40.

Construction and Cloning of Antibody H1L1

The synthetic antibody H1L1 was constructed as follows: CDH1 and CDL1 were separately PCR amplified from the sequencing vector and cloned into cloning vector pGEM-T easy (Promega Corporation) to facilitate DNA sequencing. For this 3 µg PCR product was prepared for restriction using QIAquick PCR purification spin columns (Qiagen, UK) according to the manufacturers instructions. DNA was eluted from the spin column in 40 µL buffer EB. Purified PCR product (2 µL) was mixed with 1 µL pGEM-T easy vector, 6 µL water and 1 µL DNA ligase and the mixture ligated for 1 h at room temperature. Ligations were then transformed into electrocompetent *E. coli* TG1 cells (Stratagene) by electroporation, and plated out onto agar plates containing Ampicillin 100 µg ml$^{-1}$ IPTG (100 µM) and X-gal (0.006% w/v). Colonies were allowed to grow overnight at 37° C. and then stored at 4° C. Recombinant colonies are identified as white colonies on this media.

This gave an antibody having the general structure:

S Tag-CDH1-Linker-CDL1-His Tag with the amino acid sequence of SEQ ID NO: 41 with an N-terminal S-Tag and a C-terminal His-Tag.

Identification of the Target for Antibody H1L1—Acetyl-CoA Acetyltransferase (Thiolase)

Materials and Methods

Sample Preparation:

*Clostridium difficile* cells (NCTC 11204) grown on blood agar plates were suspended in 10 mM of PBS (phosphate buffered saline) and sonicated for 5×1 minute on ice. The cell lysate was centrifuged at 13000 rpm for 5 minutes and 300 µl of the supernatant was precipitated in 20 mL 10% trichloroacetic acid and 20 mM DTT (dithiothreitol) in cold acetone for 45 minutes. The proteins were recovered by centrifugation and the pellet was washed three times with cold acetone containing 20 mM DTT.

2D-gel Electrophoresis:

The protein pellet was dissolved in sample rehydration solution (7 M urea, 2 M thiourea, 3% (w/v) CHAPS, 0.002% bromophenol blue in water) and diluted with the same solution for isoelectric focusing. Isoelectric focusing was performed using a Zoom IPGRunner (RTM) System (Invitrogen Ltd, Carlsbad, Calif., USA) over a non-linear pH range of 3-10 (7 cm) for a total of 1700 Vh, loading approximately 15 µg of protein on each strip. Prior to the second dimension separation the strips were equilibrated for 15 minutes in equilibration buffer (50 mM Tris-HCl pH 8.8, 6 M urea, 30% glycerol, 2% (w/v) SDS, 0.002% bromophenol blue in water) containing 65 mM DTT and then in the same buffer containing 125 mM iodoacetamide for another 15 minutes.

The second dimension separation was carried out using NuPage 4-12% Bis-TrisZoom gels and MOPS buffer (Invitrogen Ltd, Carlsbad, Calif., USA). The proteins were trans-blotted onto Invitrolon PVDF membrane (Invitrogen Ltd, Carlsbad, Calif., USA) and blocked in 5% skimmed milk in 0.1% Tween20 in 10 mM PBS for 1 hour.

Immunoblotting:

To identify the target of antibody H1L1, the membrane was incubated for 1 hour with purified H1L1 antibody in 5% skimmed milk in 0.1% Tween20 in 10 mM PBS. After washing, an anti-His antibody conjugated with horse radish peroxidase (Santa Cruz Biotechnologies) was used, diluted at a ratio of 1:500 with 0.1% Tween20 in 10 mM PBS, to detect bound H1L1. After washing with 0.1% Tween20 in 10 mM PBS the blot was developed using ECL (Amersham biosciences, Little Chalfont, UK).

To visualise targets for IgG antibodies in patients infected with *Clostridium difficile*, membranes were incubated for 1 hour with serum diluted 1:20-1:50 with 0.1% Tween20 in 10 mM PBS. Anti IgG-antibody conjugated with horse radish peroxidase (for ECL) or alkaline phosphatase (Sigma) where the membrane was developed using SigmaFast (RTM) 5-bromo-4-chloro-3-indolyl phosphate/nitro blue tetrazolium tablets (Sigma) was used.

Electrospray-Mass Spectrometry:

Protein bands or spots cut out from the gel were washed in 25 mM ammonium bicarbonate for 10 minutes and dehydrated using 25 mM ammonium bicarbonate:acetonitrile 1:2 for 15 minutes. After repeating the wash with ammonium bicarbonate and the dehydration step, the gel pieces were dried down in a SpeedVac (RTM). Small volumes of trypsin (10 µg/ml in 25 mM ammonium bicarbonate) were added until gel pieces returned to their original size and a small amount of 25 mM ammonium bicarbonate was added to keep the gel pieces wet during digestion. The samples were digested for 4.5 hours at 37° C. and the peptides extracted for 15 minutes by adding 80 µl acetonitrile. The supernatant was dried in a SpeedVac until all the acetonitrile had evaporated. The sample was desalted using C-18 Zip-Tips (Millipore) and analysed using nano-spray time-of-flight mass spectrometry (Q-TOF, Micromass, Manchester, Uk)

Results:

Isolation of Target for Antibody H1L1 Using 2D Gels and Immunoblotting.

2D gels combined with immunoblotting were used to pinpoint the antigen on the 2D gel. Two blots where compared, one using the serum from the patient whose most abundant antibody was the template for H1L1 and one using the expressed and purified H1L1. Both reacted to the same protein spot. The same protein was antigenic in four patients who had recovered from diarrhoea due to *C. difficile*.

Isolation of Target Protein Using a Column Method

A clinical isolate of *C. difficile* (referred to herein as strain CD 14000287, isolated from a *C. difficile* infected patient) was grown anaerobically in brain heart infusion broth supplemented with thioglycolic acid and L-cysteine-HCl for 48 hours at 37° C. The cell suspension was centrifuged in a Sorval RC-3B centrifuge at 5000 rpm for 20 minutes to pellet the cells and the cell pellet was washed once with PBS and re-centrifuged as above. The washed cell pellet was resuspended in PBS and stored at −20° C. until further use. A 2 ml aliquot of the frozen cell suspension was thawed and centrifuged at 14000 rpm for 5 minutes on a benchtop microfuge to pellet the cells, and the pelleted cells were resuspended in 4 ml of 6 M guanidine-HCl pH 8.0. The guanidine extracted protein was clarified by centrifugation at 45000 rpm on a Beckman L8-70M ultracentrifuge for 1 hour at 20° C. The supernatant was dialysed at room temperature against three times 2 litres of 20 mM sodium carbonate buffer pH 9.5 to exchange the extracted protein into a compatible buffer for the AminoLink (supplied by Perbio) column. 2 ml of an H1L1 antibody solution (~2 mg/ml) in 20 mM sodium carbonate pH 9.5 was covalently coupled to the AminoLink resin equilibrated with 20 mM sodium carbonate pH 9.5 in a prepacked 2 ml column following the manufacturer's instructions (Perbio). The *C. difficile* antigen containing extract (1.5 ml) was then applied to the covalently coupled H1L1 column and incubated with the resin for 1 hour at room temperature. Unbound material was washed through the column with 12 ml of 20 mM sodium carbonate buffer pH 9.5 and the bound antigen eluted by applying 8 ml of 0.1 M glycine buffer pH 2.5-3.0. The eluted protein was neutralised with 1 M Tris pH 9.0 prior to concentration on an Amicon 15 ml concentrator adaptor to ~200 µl. This concentrated protein material was then analysed by 10% (w/v) SDS-PAGE and visualised by Coomassie Blue staining. The H1L1 interacting protein band was then identified by mass spectrometry.

Identification of Isolated Protein Using Mass Spectrometry

The protein band or spot was cut out of the gel and digested at 37° C. with trypsin. The samples were analysed using nano electrospray time-of-flight mass spectrometry, which gave the sequence of SEQ ID NO: 42.

The same peptide was found in the samples from the 2D gel experiments as from the protein isolated using the column based method.

Searching the *Clostridium difficile* genome using BLAST search available via the Internet at a Web site operated by the Sanger Institute gives SEQ ID NO: 43 as a match.

Theoretical pI: 5.74 Molecular weight: 43430.30 Da which correlates well with the location of the protein on the 2D gel where the molecular weight was approximately 44 kD and pI 5.5-6.

Using the protein sequence of SEQ ID NO: 43 in a protein-protein NCBI BLAST search available via the Internet at a Web site operated by the US National Library of Medicine using default settings reveals high similarity to acetyl-CoA-acetyltransferase (thiolase) accession number NP.sub.—349376 with 68% identity over 391 amino acids.

Cloning of the Acetyl-CoA Acetyltransferase

For cloning and expression in *E. coli* the sequence encoding the acetyl-CoA acetyltransferase was PCR amplified directly from *C. difficile* genomic DNA, and prepared using DNeasy spin columns (Qiagen) according to the manufacturer's instructions.

PCR primers used were identified and designed by direct comparison with the *C. difficile* genomic DNA sequence encoding the candidate match for the acetyl-CoA acetyltransferase, and are SEQ ID NOs: 44 and 45, synthesized by SIGMA Genosys.

Amplification was carried out using Taq DNA polymerase (Invitrogen) allowing direct ligation-independent cloning into the expression vector pBAD-TA (Invitrogen), adding a C-terminally fused $His_6$-tag to the expressed acetyl-CoA acetyltransferase under the control of the Arabinose-inducible promoter araBAD. The cloning mix was transformed in to the expression strain TOP10 (Invitrogen) and recombinants were identified using SDS-PAGE and immunoblotting using a monoclonal anti-His-tag peroxidase-conjugate antibody (SIGMA). The resulting plasmid is referred to herein as pThioll.

Expression and Purification of the Acetyl-CoA Acetyltransferase

For over-expression of the 6-His-tag thiolase fusion protein, *E. coli* strain TOP10 (pThioll) was grown to late exponential phase ($OD_{600}$ 1.0 at 37° C. with shaking at 200 rpm) and protein expression was induced by the addition of Arabinose to a final concentration of 0.2%. After a further 240 minutes growth, bacteria were harvested by centrifugation (500 g, 10 minutes 4° C.) and the pellet was resuspended in lysis buffer (6 M Guanidine Hydrochloride, 50 mM Tris-HCl pH 8) at 1/20 the starting volume and solubilized by mixing for 1 hour at room temperature. Insoluble material was removed by a further centrifugation step (10000 g, 10 minutes at room temperature) and the supernatant applied to a Qiagen spin-prep Ni-NTA column following the manufacturer's instructions. The column was washed three times with 600 μl of lysis buffer followed by three washes with 600 μl of wash buffer 1 (8 M Urea, 50 mM Tris/HCl pH 8) and three times with 600 μl of wash buffer 2 (8 M Urea, 50 mM Tris HCl pH 8, 25 mM Imidazole). The His-Tag protein was eluted from the column with 100 μl of elution buffer (8 M Urea, 50 mM Tris/HCl pH 8, 250 mM Imidazole), the elution step was repeated and both fractions pooled. Samples were analysed by SDS-PAGE.

Testing Antibody H1L1 Against Cloned Acetyl-CoA Acetyl Transferase

Cloned and purified acetyl-CoA acetyl transferase was mixed 1:1 with loading buffer and DTT and put on heating block at 90° C. for 5 minutes. 5-15 μl was separated for 35 minutes on a 10% BisTris gel (Invitrogen) using NuPAGE-MES SDS running buffer (Invitrogen).

The proteins were transblotted onto Invitrolon PVDF membrane (Invitrogen Ltd, Carlsbad, Calif., USA) and blocked in 5% skimmed milk in 0.1% Tween20 in 10 mM PBS for 1 hour. The membrane was incubated with H1L1 at 1:10 (concentration approximately 400 μg/ml) in 0.1% Tween20 in 10 mM PBS for 1 hour. Washed three times for 5 minutes with 0.1% Tween20 in 10 mM PBS and then incubated for one hour with S-protein HRP conjugate (Novagen) at 1:1000. The blot was developed using Sigma-Fast DAB stain and shows a strong response to the thiolase band located just under the 50 kD marker.

Therefore, antibody from patients with *C. difficile* infection is focussed against *C. difficile* acetyl-CoA acetyl transferase and synthetic antibody constructed from the dominant light and heavy chain CDRs of those patients is specific against the *C. difficile* acetyl-CoA acetyl transferase. Therefore, *C. difficile* acetyl-CoA acetyl transferase is a strong antigen and antibody H1L1 is useful in binding it.

Conserved Epitope

There are three consecutive enzymes in the butanol/butyrate-producing pathway of *Clostridium acetobutylicum* which are also present on the *Clostridium difficile* chromosome. These have been found to react with a rabbit anti-serum raised against supernatant proteins from *Clostridium difficile* (Mullany P et al., FEMS Microbiol Lett., 1994 Nov. 15; 124(1): 61-7; PMID: 8001771).

Assuming the enzymes share a conserved epitope, the only homologous region can be found at residue 9-12 in thiolase (accession number P45362) which is present in crotonase (accession number P45361) residues 5-8, and this conserved sequence is SEQ ID NO: 47.

*Enterococcus faecium* and *Clostridium difficile* Combination Drug MIC

Pre-Assay Preparation

The organisms were cultured onto a Columbia Blood Agar plate (CBA) to achieve single colonies and incubated at 37° C. for 24 hours (*E. faecium*) or anaerobically for 48 hours (*C. difficile*).

Antimicrobial agents were prepared according to NCCLS methodology (M7-6A), giving a total of 14 concentrations for vancomycin and gentamicin and 11 concentrations for H1L1. The initial dilutions of vancomycin and gentamicin were made in $dH_2O$, H1L1 was initially diluted in Formulation Buffer (In 100 ml: 3.484 g Arginine (200 mM), 3.006 g Urea (0.5 M), pH 9.5). Subsequent dilutions were made in the appropriate growth medium for the organism being used. The agents were stored in aliquots at −20° C. and thawed on the day of use.

Concentrations were twice the final concentration required.

1. Medium Preparation

*E. faecium* Medium—Cation-adjusted Mueller Hinton Broth (NCCLS M7-6A): To 1 litre Mueller Hinton Broth (OXOID, MHB), 2 ml of 10 mg/ml $CaCl_2$ and 500 μl of 10 mg/ml $MgCl_2$ were added C. difficile Medium—
(1) Supplemented *Brucella* Broth (NCCLS M11-A5): To 900 ml Brucella Broth powder (SIGMA), 1 ml Hemin (5 mg/ml) and 1 ml Vitamin K (1 mg/ml) were added. Post autoclaving 100 ml Lysed horse blood (5%) was added.
(2) Reinforced clostridial medium (RCM) was prepared according to the manufacturers instructions: 38 g in 1 litre $dH_2O$.

2. MIC Plate Preparation—Table 1

Drug 1—vancomycin or gentamicin (final concentration range 0.0625 μg/ml to 512 μg/ml)

In a U-shaped 96 well microtitre plate: twice the required concentration of vancomycin or gentamicin (50 μl) is added left to right along the first row of the microtitre plate leaving the final well blank. This was repeated for the other rows using 2-fold decreasing concentrations of vancomycin.

Drug 2—H1L1 antibody (final concentration range 0.25 μg/ml to 256 μg/ml)

H1L1 (50 ml) is added down the columns. Twice the required concentration is added down the first column. This was repeated for the other columns moving along the plate (left to right) 2-fold decreasing concentrations of H1L1. The last column is left blank The final column contains 100 μl of growth medium only Continuing concentrations of vancomycin and gentamicin were performed in the same manner as above but on a second microtitre plate. H1L1 concentrations were exactly the same as above, as were the Media only control in column 12.

Inoculum Preparation—Direct Colony Suspension

The inoculum was prepared immediately prior to use of the bacteria.

A direct colony suspension was made by resuspending colonies from an 18 to 24 hour (*E. faecium*) or 48 hour (*C. difficile*) agar plate into the appropriate growth medium or sterile saline.

This was adjusted to 0.5 MacFarlands standard then diluted 1:10 in growth medium (approximately $1\times10^7$ cfu/ml) according to NCCLS M7-6A (*E. faecium*) and NCCLS M11-A5 (*C. difficile*).

Plate Inoculation

5 μl of the 1:10 inoculum suspension prepared as above was used to inoculate each well (final inoculum $5\times10^4$ cfu/ml).

The plate was inoculated from well 12 to well 1.

Incubation

The plates were incubated at 37° C. for 24 hours (*E. faecium*) or anaerobically for 48 hours (*C. difficile*).

To check the inoculum 10 μl from the growth control was diluted in 10 ml sterile saline (1:1000), and 100 μl was plated onto a CBA plate and incubated at 37° C. for 24 hours (*E. faecium*) or anaerobically for 48 hours (*C. difficile*). Fifty colonies were equivalent to $5\times10^4$ cfu/ml.

Reading Results

The MIC was taken as the lowest concentration of drug that substantially inhibited the growth of the organism.

The FIC (fractional inhibitory concentration) was calculated for each drug by dividing the MIC in the presence of the second drug by the MIC in its absence. For each combination this produced two fractions, which were summated to produce the FICI (fractional inhibitory concentration index): synergy was defined by a value of <=0.5, indifference was defined by a value of >0.5 to <4 and antagonism was defined by a value of >=4.0

Results

These results demonstrate synergy between H1L1 and vancomycin and gentamicin

Conclusions

These results demonstrated synergy between both (i) H1L1 and vancomycin, and (ii) H1L1 and gentamicin versus *C. difficile* 14000287 and *C. difficile* NCTC 11204. It showed synergy between Vancomycin and H1L1 in Vancomycin resistant *Enterococcus faecium*.

Growth of *Clostridium difficile* in the Presence of Variable Short Chain Fatty Acids (SCFA) and H1L1 Antibody Concentrations SCFA Preparation The three SCFAs used were acetate, propionate and butyrate.

Each was prepared to a concentration of 1 M as follows:

Sodium acetate FW 82.03-82.03 g in 1 litre $dH_2O$

Sodium butyrate FW 110.09-110.09 g in 1 litre $dH_2O$

Sodium propionate FW 96.06-96.06 g in 1 litre $dH_2O$

The three solutions were combined in a ratio of 70:20:10 respectively. Therefore, in the final solution the concentrations were sodium acetate 0.7 M, sodium butyrate 0.2 M and sodium propionate 0.1 M. The final concentration of total SCFA was 1 M.

From this stock solution concentrations of 5, 10, 20, 30, 40 and 50 mM total SCFA were prepared using reinforced clostridial medium (RCM, DIFCO).

Medium Preparation

Reinforced clostridial medium (RCM) was prepared according to the manufacturers instructions: 38 g in 1 litre $dH_2O$ Growth Curve Day Before Assay Cultures were only removed from anaerobic conditions immediately prior to use. Exposure to aerobic conditions did not exceed 30 minutes An overnight suspension of *C. difficile* was made by inoculation 10 ml of RCM medium with colonies from a 48 hour old Columbia Blood Agar plate of the organism. The suspension was incubated for 24 hours at 37° C. under anaerobic conditions.

Day of Assay

Control Plate

In a flat-bottomed 96 well microtitre plate control solutions (200 μl) were placed in the wells as outlined below in Table 4. Each control used 3 wells.

Test Plate

In a flat-bottomed 96 well microtitre plate (rows labelled A-H, columns labelled 1-12) test solutions (100 μl) were placed in the wells as detailed below. The two test solutions, SCFA plus H1L1, give a combined volume of 200 μl. Each test used 2 wells. Wells in row A contained 50 mM SCFA; in row B, 40 mM SCFA; in row C, 30 mM SCFA; in row D, 20 mM SCFA; in row E, 10 mM SCFA; in row F, 0.5 mM SCFA. Wells in columns 1 and 2 contained 16 μg/ml H1L1; in columns 3 and 4, 8 μg/ml H1L1; in columns 5 and 6, 4 μg/ml H1L1; in columns 7 and 8, 2 μg/ml H1L1; in columns 9 and 10, 1 μg/ml H1L1; in columns 11 and 12, 0.5 μg/ml H1L1. Row G was empty. 200 μl RCM was placed into all the wells in row H as a growth control for the plate.

Inoculum Preparation

Cultures were only removed from anaerobic conditions immediately prior to use. Exposure to aerobic conditions did not exceed 30 minutes.

The overnight suspension, culture at late log phase, was used to inoculate the microtitre plates. 20 μl (approx 10% inoculum) was added to all the wells, except for the media/negative control on the control plate.

Plates were incubated at 37° C. under anaerobic conditions for 24 hours.

Optical density readings ($OD_{600}$ nm) were made at time points zero and 24 hours. Average $OD_{600}$ nm readings were determined.

Results

Controls—see Table 5.

TABLE 1

Drug concentrations at this stage will be half the concentration that was put into the wells (50 μl + 50 μl = 1:2 dilution).

| | 1 | 2 | 3 | 4 | 5 | 6 | 7 | 8 | 9 | 10 | 11 | 12 |
|---|---|---|---|---|---|---|---|---|---|---|---|---|
| A | A1 | A2 | A3 | A4 | A5 | A6 | A7 | A8 | A9 | A10 | A11 | Media only |
| B | B1 | B2 | B3 | B4 | B5 | B6 | B7 | B8 | B9 | B10 | B11 | Media only |
| C | C1 | C2 | C3 | C4 | C5 | C6 | C7 | C8 | C9 | C10 | C11 | Media only |
| D | D1 | D3 | D4 | D4 | D5 | D6 | D7 | D8 | D9 | D10 | D11 | Media only |
| E | E1 | E2 | E3 | E4 | E5 | E6 | E7 | E8 | E9 | E10 | E11 | Media only |
| F | F1 | F2 | F3 | F4 | F5 | F6 | F7 | F8 | F9 | F10 | F11 | Media only |
| G | G1 | G2 | G3 | G4 | G5 | G6 | G7 | G8 | G9 | G10 | G11 | Media only |
| H | H1 | H2 | H3 | H4 | H5 | H6 | H7 | H8 | H9 | H10 | H11 | Media only |

A, B, etc. = Vancomycin or gentamicin
1, 2, 3 etc. = +H1L1

TABLE 2

| Species | Agent | MIC (μg/ml) of each agent Alone | MIC (μg/ml) of each agent Combination | FIC (μg/ml) | FICI | Outcome |
|---|---|---|---|---|---|---|
| Clostridium difficile NCR 1104 (Brucella broth) | Vancomycin | 1 | 0.125 | 0.125 | 0.125 | Synergy |
| | H1L1 | 512 | 0.25 | 0.0004 | | |
| Enterococcus faecium | Vancomycin | 128 | 16 | 0.12 | 0.37 | Synergy |
| | H1L1 | 512 | 128 | 0.25 | | |

Conclusions—
1. No effect of 10, 20, 30, and 40 mM of SCFA on its own, but some decrease with 50 mM of SCFA.
2. No effect with 0.5, 1, 2 4, and 8 μg/ml of H1L1 but inhibition with 16 μg/ml of H1L1.

Tests—see Table 6.

Conclusions—

Indifference with 1, 2 and 4 μg/ml of H1L1 and 5 mM of SCFA (data not shown). Synergy with 8 μg/ml of H1L1 and SCFA from 10-50 mM with optical density at 24 hours falling to a range of 0.296-0.330. The effect was most obvious with 16 μg/ml of H1L1 and 50 mM of SCFA.

TABLE 3

| Species | Agent | MIC (μg/ml) of each agent Alone | MIC (μg/ml) of each agent Combination | FIC (μg/ml) | FICI | Outcome |
|---|---|---|---|---|---|---|
| C. difficile 14000287 (Brucella broth) | Gent | 8 | 2 | 0.25 | 0.266 | Synergy |
| | H1L1 | 512 | 8 | 0.0156 | | |
| C. difficile NCTC 11204 (RCM) | Gent | 16 | 4 | 0.25 | 0.375 | Synergy |
| | H1L1 | 512 | 64 | 0.125 | | |

TABLE 4

|   | 1 | 2 | 3 | 4 | 5 | 6 | 7 | 8 | 9 | 10 | 11 | 12 |
|---|---|---|---|---|---|---|---|---|---|----|----|----|
| A | RCM no inoculum | | | RCM + inoculum | | | | | | | | |
| B | RCM + 50 mM SCFA | | | RCM + 40 mM SCFA | | | RCM + 30 mM SCFA | | | RCM + 20 mM SCFA | | |
| C | RCM + 10 mM SCFA | | | RCM + 5 mM SCFA | | | | | | | | |
| D | RCM + 16 µg/ml H1L1 | | | RCM + 8 µg/ml H1L1 | | | RCM + 4 µg/ml H1L1 | | | RCM + 2 µg/ml H1L1 | | |
| E | RCM + 1 µg/ml H1L1 | | | RCM + 0.5 µg/ml H1L1 | | | | | | | | |
| F | | | | | | | | | | | | |
| G | | | | | | | | | | | | |
| H | | | | | | | | | | | | |

TABLE 5

| Experiment No | H1L1 (µg/ml) | SCFA (mM) | Mean Optical Density at 24 Hours |
|---|---|---|---|
| 1 | — | — | 0.452 |
| 2 | — | 5 | 0.460 |
| 3 | — | 10 | 0.429 |
| 4 | — | 20 | 0.452 |
| 5 | — | 30 | 0.480 |
| 6 | — | 40 | 0.440 |
| 7 | — | 50 | 0.370 |
| 8 | 0.5 | — | 0.450 |
| 9 | 1 | — | 0.440 |
| 10 | 2 | — | 0.440 |
| 11 | 4 | — | 0.440 |
| 12 | 8 | — | 0.420 |
| 13 | 16 | — | 0.334 |

TABLE 6

| Experiment No | H1L1 (µg/ml) | SCFA (mM) | Mean Optical Density at 24 Hours |
|---|---|---|---|
| 1 | 8 | 10 | 0.310 |
| 2 | 16 | 10 | 0.308 |
| 3 | 8 | 20 | 0.296 |
| 4 | 16 | 20 | 0.228 |
| 5 | 8 | 30 | 0.305 |
| 6 | 16 | 30 | 0.308 |
| 7 | 8 | 40 | 0.310 |
| 8 | 16 | 40 | 0.303 |
| 9 | 8 | 50 | 0.330 |
| 10 | 16 | 50 | 0.281 |

---

What is claimed is:

1. An isolated antibody or antigen binding fragment thereof that binds acetyl-coA-acetyltransferase of *Clostridium difficile*, the antigen or antigen binding fragment thereof comprising:
    (i) a heavy chain, wherein complementarity determining region 1 comprises the amino acid sequence of SEQ ID NO: 2, complementarity determining region 2 comprises the amino acid sequence of SEQ ID NO: 3 and complementarity determining region 3 comprises the amino acid sequence of SEQ ID NO: 4, and
    (ii) a light chain, wherein complementarity determining region 1 comprises the amino acid sequence of SEQ ID NO: 17, complementarity determining region 2 comprises the amino acid sequence of SEQ ID NO: 18 and complementarity determining region 3 comprises the amino acid sequence of SEQ ID NO: 19.

2. The antibody or antigen binding fragment thereof according to claim 1, wherein the heavy chain comprises the amino acid sequence of SEQ ID NO: 1.

3. The antibody or antigen binding fragment thereof according to claim 1, wherein the light chain comprises the amino acid sequence of SEQ ID NO: 16.

4. The antibody or antigen binding fragment thereof according to claim 1, wherein the antibody comprises the amino acid sequence of SEQ ID NO: 41.

* * * * *